(12) United States Patent
Kim

(10) Patent No.: US 10,349,832 B2
(45) Date of Patent: Jul. 16, 2019

(54) METHOD OF DETECTING BOUNDARY BETWEEN IRIS AND SCLERA

(71) Applicant: 3E CO., LTD., Seongnam-si, Gyeonggi-do (KR)

(72) Inventor: Min Ho Kim, Seongnam-si (KR)

(73) Assignee: 3E CO., LTD., Seongnam-si (KR)

( * ) Notice: Subject to any disclaimer, the term of this patent is extended or adjusted under 35 U.S.C. 154(b) by 229 days.

(21) Appl. No.: 15/632,876

(22) Filed: Jun. 26, 2017

(65) Prior Publication Data

US 2018/0168446 A1  Jun. 21, 2018

(30) Foreign Application Priority Data

Dec. 21, 2016 (KR) .......................... 10-2016-0175219

(51) Int. Cl.
```
A61B 3/12      (2006.01)
G06K 9/00      (2006.01)
G06K 9/46      (2006.01)
G06K 9/52      (2006.01)
G07C 9/00      (2006.01)
A61B 5/117     (2016.01)
G06F 21/32     (2013.01)
A61B 5/1171    (2016.01)
```
(52) U.S. Cl.
CPC .............. *A61B 3/12* (2013.01); *A61B 5/1171* (2016.02); *G06F 21/32* (2013.01); *G06K 9/00597* (2013.01); *G06K 9/00906* (2013.01); *G06K 9/4609* (2013.01); *G06K 9/52* (2013.01); *G07C 9/00158* (2013.01); *A61B 5/117* (2013.01); *G06K 9/00* (2013.01)

(58) Field of Classification Search
None
See application file for complete search history.

(56) References Cited

U.S. PATENT DOCUMENTS

| | | | |
|---|---|---|---|
| 4,908,872 A * | 3/1990 | Toriu | ................... G06K 9/4609 382/197 |
| 7,869,626 B2 | 1/2011 | Ko et al. | |
| 8,958,608 B2 | 2/2015 | Santos-Villalobos et al. | |

FOREIGN PATENT DOCUMENTS

| | | |
|---|---|---|
| JP | 2009-200874 A | 9/2009 |
| KR | 10-2008-0025610 A | 3/2008 |
| KR | 10-2011-0078468 A | 7/2011 |

OTHER PUBLICATIONS

Notice of Allowance issued by the Korean Intellectual Property Office for corresponding Korean Patent Application No. 10-2016-0175219, dated Jul. 19, 2017.
Park et al., "An Efficient Method of Extracting Iris Area Using the Inner Canthus", Korea Information Science Society, Oct. 2003, pp. 544-546, with English abstract.

\* cited by examiner

*Primary Examiner* — Chan S Park
*Assistant Examiner* — Elisa M Rice
(74) *Attorney, Agent, or Firm* — Patent Office of Dr. Chung Park

(57) ABSTRACT

A method of detecting the boundary between the iris and the sclera, particularly, a method of detecting the boundary between the iris and the sclera from part of a captured image of a user's eye area, is provided. According to this method, the boundary between the iris and the sclera can be quickly and precisely detected, compared to when using an existing circular boundary detector.

10 Claims, 10 Drawing Sheets

METHOD OF DETECTING BOUNDARY BETWEEN IRIS AND SCLERA

This application claims priority to Korean Patent Application No. 10-2016-0175219, filed on Dec. 21, 2016, and all the benefits accruing therefrom under 35 U.S.C. § 119, the disclosure of which is incorporated herein by reference in its entirety.

BACKGROUND

1. Field

The present disclosure relates to a method of detecting the boundary between the iris and the sclera, and more particularly, to a method of detecting the boundary between the iris and the sclera from part of a captured image of a user's eye area.

2. Description of the Related Art

Recently, as the protection of person information becomes an issue of importance online and offline, biometric technology, among other various security technologies, has increasingly attracted attention. Biometric technology refers to technology for authenticating a user by using each individual's unique biometric information such as fingerprints, irises, and veins.

Iris recognition technology, which is a type of biometric technology, uses each individual's unique iris information in user authentication.

In order to perform user authentication using iris information, an iris area needs to be detected first from a captured image of a user's eye area. As pretreatment for the detection of the iris area, the center of the pupil needs to be detected from the captured image of the user's eye area, and the distance between the detected pupil center and the boundary between the iris and the sclera needs to be calculated.

FIG. 1 is a schematic view illustrating the distance between the center of the pupil and the boundary between the iris and the sclera.

Referring to FIG. 1, a captured image 10 of a user's eye area includes a pupil area 20, an iris area 30, and a sclera area 40.

The iris area 30 is an area to be used in user authentication. In order to acquire only data of the iris area 30, the center of the pupil area 20 needs to be detected, a distance d between the detected center of the pupil area 20 and the boundary between the iris area 30 and the sclera area 40 needs to be calculated, and image data needs to be acquired from an entire circular region having the distance d as its radius, except for the pupil area 20.

Conventionally, a circular boundary detector is used to calculate the distance d between the detected center of the pupil area 20 and the boundary between the iris area 30 and the sclera area 40. However, a conventional boundary detection method using the circular boundary detector depends on global image search, and thus, it takes a long time to calculate the distance d between the detected center of the pupil area 20 and the boundary between the iris area 30 and the sclera area 40.

The conventional boundary detection method using the circular boundary detector is hardly efficient, especially considering that the amount of time that it takes to perform biometric authentication is one of the most important factors for evaluating the performance of a user authentication system using biometric information.

Accordingly, a detection algorithm capable of quickly and precisely calculating the distance from the center of the pupil area 20 to the boundary between the iris area 30 and the sclera area 40 is needed.

SUMMARY

Exemplary embodiments of the present disclosure provide an iris radius measurement method capable of calculating the distance between the center of the pupil and the boundary between the iris and the sclera.

However, exemplary embodiments of the present disclosure are not restricted to those set forth herein. The above and other exemplary embodiments of the present disclosure will become more apparent to one of ordinary skill in the art to which the present disclosure pertains by referencing the detailed description of the present disclosure given below.

According to an exemplary embodiment of the present invention provides method of detecting the boundary between the iris and the sclera, the method comprising: receiving a captured image of a user's eye area; selecting pixels included in a predefined region of the received image; selecting pixels in the same direction with respect to the center of the pupil from among the selected pixels from the predefined region; creating one or more pixel groups by selecting a predefined number of pixels from among the selected pixels in the same direction with respect to the center of the pupil; calculating a feature value of each of the pixel groups by comparing brightnesses of each pair of adjacent pixels included in a corresponding pixel group; selecting a pixel group having a largest feature value and calculating a first sum of brightnesses of pixels to the left of each pixel in the selected pixel group and a second sum of brightnesses of pixels to the right of a corresponding pixel, starting from a pixel at the center of the selected pixel group and proceeding in sequence to the pixels to the left of the center pixel; and determining one or more pixels having a larger first sum than a second sum as pixels corresponding to the boundary between the iris and the sclera.

According to an exemplary embodiment of the present invention, wherein the selecting the pixels included in the predefined region comprises selecting pixels in a range of a direction $\theta_\alpha°$ to a direction $\theta_\beta°$ with respect to the center of the pupil at intervals of a predefined angle and selecting a number of pixels corresponding to a predetermined length from among the selected pixels in the range of the direction $\theta_\alpha°$ to the direction $\theta_\beta°$ with respect to the center of the pupil, starting from a pixel spaced a predetermined distance from the center of the pupil.

According to an exemplary embodiment of the present invention, the method further comprises creating a matrix by arranging the brightnesses of pixels in the direction $\theta_\alpha°$ with respect to the center of the pupil in an uppermost row of the matrix and sequentially arranging the brightnesses of pixels in directions rotated from the direction $\theta_\alpha°$ at intervals of the predefined angle in rows below the uppermost row so that the brightnesses of pixels in the direction $\theta_\beta°$ with respect to the center of the pupil can be arranged in a lowermost row of the matrix, and arranging the brightnesses of pixels closest to the center of the pupil in a leftmost column of the matrix and sequentially arranging the brightnesses of pixels less close to the center of the pupil in columns to the right of the leftmost column so that the brightnesses of pixels most distant from the center of the pupil can be arranged in a rightmost column of the matrix.

According to an exemplary embodiment of the present invention, wherein the selecting the pixels in the same direction with respect to the center of the pupil, comprises selecting pixels corresponding to elements included in the same row of the matrix.

According to an exemplary embodiment of the present invention, wherein the creating the pixel groups, comprises (a) creating a first pixel group by selecting a predefined number of elements from each row of the matrix, (b) creating a second pixel group by selecting elements such that some of the pixels included in the first pixel group can also be included in the second pixel group, and repeatedly performing (a) and (b) so that all the elements included in each row of the matrix can be selected at least once.

According to an exemplary embodiment of the present invention, wherein the calculating the feature value of each of the pixel groups, comprises calculating a difference between the brightness of each pixel included in each of the pixel groups and the brightness of a pixel adjacent thereto to the right, allocating a value of 1 if the calculated difference is positive and allocating a value of −1 if the calculated difference is negative, and determining a sum of all the allocated values as the feature value of each of the pixel groups.

According to an exemplary embodiment of the present invention, wherein the selecting the pixel group having the largest feature value and the calculating the first and second sums, comprise calculating a first sum of brightnesses of a predefined number of pixels to the left of each pixel and calculating a second sum of brightnesses of a predefined number of pixels to the right of a corresponding pixel.

According to an exemplary embodiment of the present invention, the method further comprises determining one or more pixels having a largest second sum-to-first sum ratio as the pixels corresponding to the boundary between the iris and the sclera.

According to an exemplary embodiment of the present invention, the method further comprises calculating differences in distance from the center of the pupil between one of the determined pixels and the other determined pixels; calculating the number of differences calculated to be smaller than a predefined threshold value for each of the determined pixels; and determining a distance between one of the determined pixels having a largest number of differences calculated to be smaller than the predefined threshold value and the center of the pupil as a distance between the center of the pupil and the boundary between the iris and the sclera.

According to an another exemplary embodiment of the present invention provide apparatus for detecting the boundary between the iris and the sclera, comprising: at least one processor; a memory loading a computer program, which is executed by the processor; and a storage storing a computer program capable of detecting the boundary between the iris and the sclera, wherein the computer program capable of detecting the boundary between the iris and the sclera, comprises: an operation of receiving a captured image of a user's eye area; an operation of selecting pixels included in a predefined region of the received image; an operation of selecting pixels in the same direction with respect to the center of the pupil from the selected pixels from the predefined region; an operation of creating one or more pixel groups by selecting a predefined number of pixels from the selected pixels in the same direction with respect to the center of the pupil; an operation of calculating a feature value of each of the pixel groups by comparing brightnesses of each pair of adjacent pixels included in a corresponding pixel group; an operation of selecting a pixel group having a largest feature value and calculating a first sum of brightnesses of pixels to the left of each pixel in the selected pixel group and a second sum of brightnesses of pixels to the right of a corresponding pixel, starting from a pixel at the center of the selected pixel group and proceeding in sequence to the pixels to the left of the center pixel; and an operation of determining one or more pixels having a larger first sum than a second sum as pixels corresponding to the boundary between the iris and the sclera.

According to exemplary embodiments of the present disclosure, the boundary between the iris and the sclera can be quickly and precisely detected, compared to a conventional circular boundary detector.

Other features and exemplary embodiments may be apparent from the following detailed description, the drawings, and the claims.

BRIEF DESCRIPTION OF THE DRAWINGS

The above and other exemplary embodiments and features of the present disclosure will become more apparent by describing in detail exemplary embodiments thereof with reference to the attached drawings, in which.

DETAILED DESCRIPTION

Figure 1:
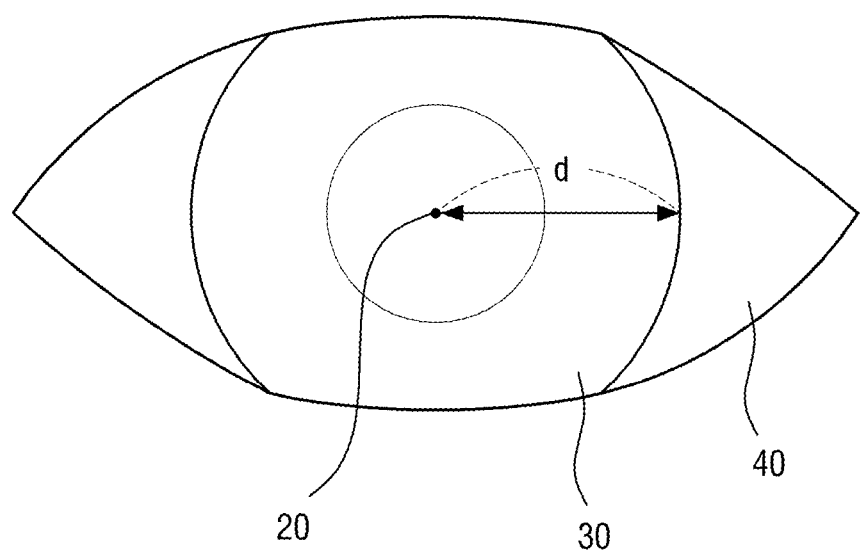
FIG. 1 is a schematic view illustrating the distance between the center of the pupil and the boundary between the iris and the sclera.

Hereinafter, exemplary embodiments of the present disclosure will be described in detail with reference to the accompanying drawings. Advantages and features of the present disclosure and methods to achieve them will become apparent from the descriptions of exemplary embodiments herein below with reference to the accompanying drawings. However, the present invention is not limited to exemplary embodiments disclosed herein but may be implemented in various different ways. The exemplary embodiments are provided for making the disclosure of the present invention thorough and for fully conveying the scope of the present invention to those skilled in the art. It is to be noted that the scope of the present invention is defined only by the claims. Like reference numerals denote like elements throughout the descriptions.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

Unless specifically mentioned otherwise, a singular form may include a plural form in the present specification. Throughout this specification, the word "comprise" and variations such as "comprises" or "comprising," will be understood to imply the inclusion of stated constituents, steps, operations and/or elements but not the exclusion of any other constituents, steps, operations and/or elements.

Figure 2:
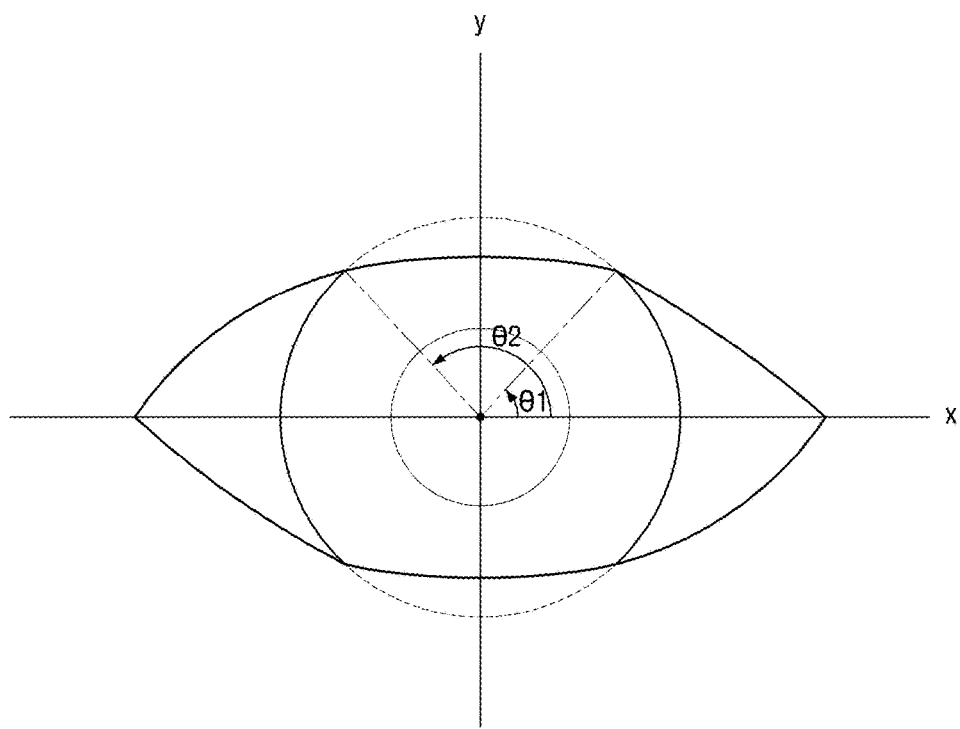
FIG. 2 is a schematic view illustrating a process of acquiring only data of part of an iris area according to an exemplary embodiment of the present disclosure.

FIG. 2 is a schematic view illustrating a process of acquiring only data of part of an iris area according to an exemplary embodiment of the present disclosure.

Referring to FIG. 2, a method of detecting the boundary between the iris and the sclera according to an exemplary embodiment of the present disclosure includes receiving a captured image of a user's eye area. The captured image of the user's eye area may include a pupil area, an iris area, and a sclera area, as illustrated in FIG. 2.

Thereafter, pixels included in a predefined region of the captured image of the user's eye area are selected. Since iris data cannot be fully acquired from upper and lower portions of the captured image of the user's eye area because of the upper and lower portions being covered by the eyelids, the predefined region may be an either side region that is not covered by the eyelids.

For example, referring to FIG. 2, part of the iris area between angles $\theta_1°$ and $\theta_2°$ with respect to an X axis is likely to be covered by the upper eyelid. Thus, it may not be appropriate to calculate the radius of the iris using iris data obtained from the part of the iris area between the angles $\theta_1°$ and $\theta_2°$ with respect to the X axis.

Accordingly, the radius of the iris may be measured using only iris data acquired from part of the iris area that is less likely to be covered by the upper or lower eyelid.

Once part of the iris area from which to acquire iris data is determined, pixel information is extracted from the determined part of the iris area.

Figure 3:
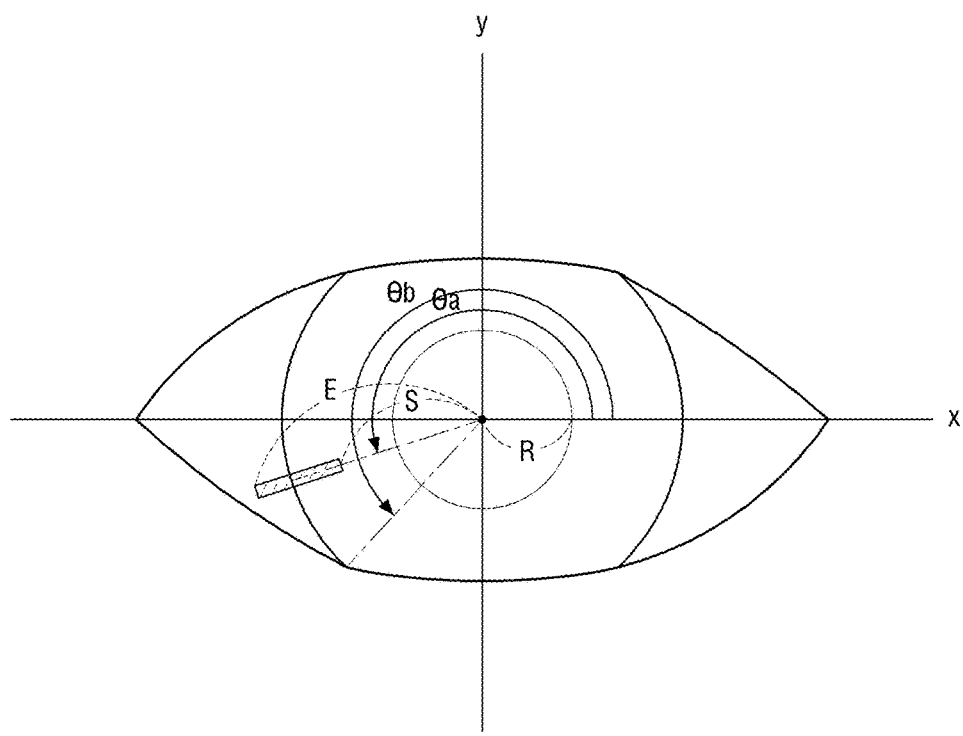
FIG. 3 is a schematic view illustrating a process of extracting pixel information from part of an iris area according to an exemplary embodiment of the present disclosure.

FIG. 3 is a schematic view illustrating a process of extracting pixel information from part of an iris area according to an exemplary embodiment of the present disclosure.

Referring to FIG. 3, in order to detect the boundary between the iris and the sclera, pixels in the same direction with respect to the center of the pupil are selected. Specifically, pixels are selected in a direction θ (where $\theta_\alpha \leq \theta \leq \theta_\beta$) with respect to the center of the pupil at intervals of a predefined angle.

For example, in a case where the predefined angle is 1°, pixels may be extracted in directions $\theta_\alpha°$, $\theta_\alpha+1°$, $\theta_\alpha+2°$, ..., $\theta_\beta°$ with respect to the center of the pupil.

However, it may be ineffective to extract all pixels in each selected direction with respect to the center of the pupil.

Thus, only a number of pixels corresponding to a predefined length may be extracted in each selected direction with respect to the center of the pupil because some of the pixels in the corresponding selected direction with respect to the center of the pupil may be unnecessary for the calculation of the distance between the center of the pupil and the boundary between the iris and the sclera.

Accordingly, only a number of pixels corresponding to the predefined length may be extracted along each selected direction with respect to the center of the pupil, starting from a pixel spaced a predetermined distance from the center of the pupil.

Specifically, as illustrated in FIG. 3, a number of pixels corresponding to a length w may be extracted along a predetermined direction with respect to the center of the pupil, starting from a pixel spaced a distance S from the center of the pupil.

The length w corresponds to the length between a starting point S and an ending point E.

The starting point S may be determined by Equation (1):

$$S = R + \frac{\text{Standard} - R}{170} \times 100, \quad E = S + w \tag{1}$$

where R denotes the radius of the pupil and "Standard" denotes a predefined constant.

Figure 4:
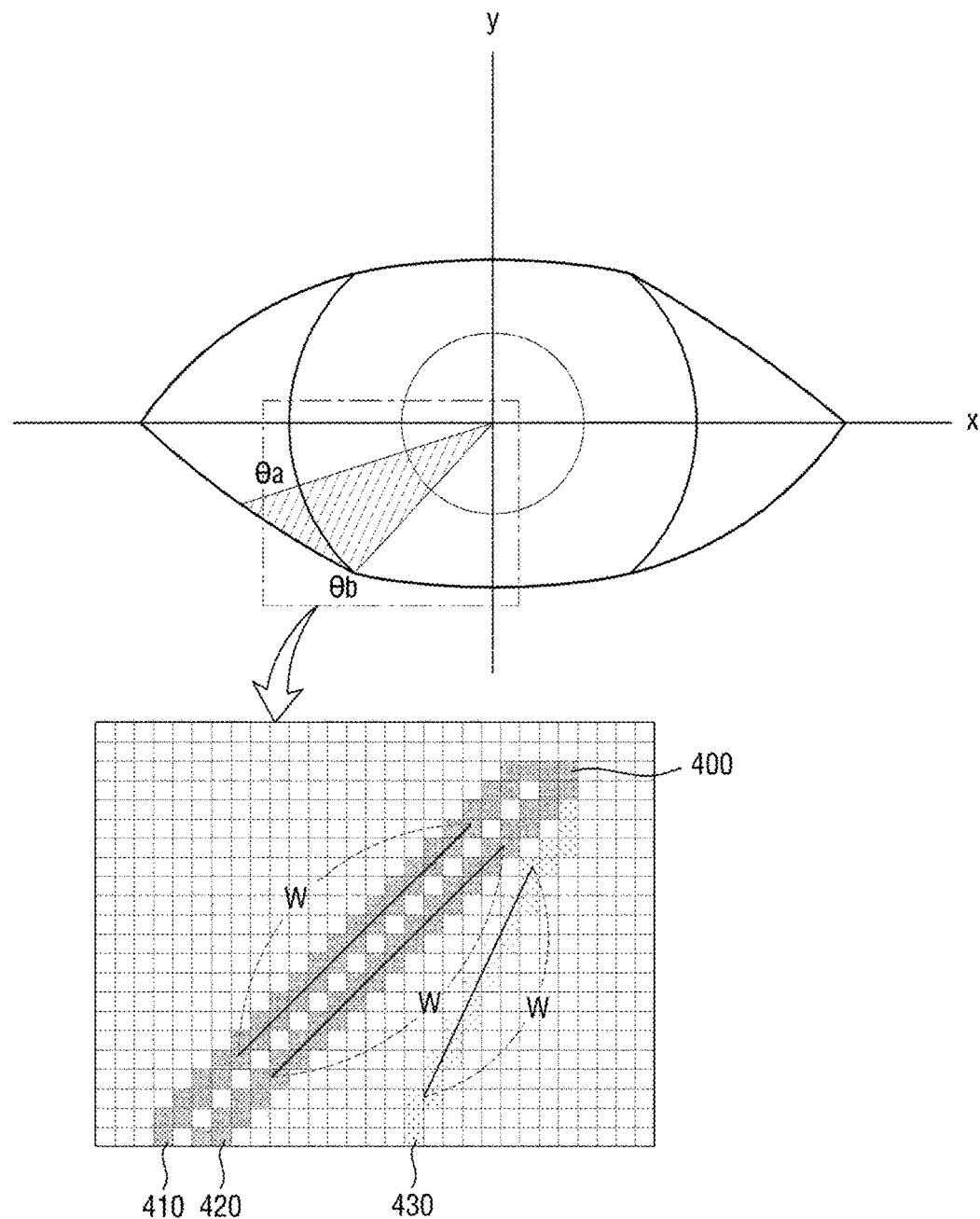
FIG. 4 is a schematic view illustrating pixels extracted from a selected area.

FIG. 4 is a schematic view illustrating pixels extracted from a selected area.

Pixels extracted by the process of FIG. 3 for calculating the distance between the center of the pupil and the boundary between the iris and the sclera are as illustrated in FIG. 4.

FIG. 4 shows only some pixels selected from the direction θ (where $\theta_\alpha \leq \theta \leq \theta_\beta$) with respect to the center of the pupil at intervals of the predefined angle. In some exemplary embodiments, only a number of pixels corresponding to the length w are selected from a plurality of pixels in each of first, second, and third direction 410, 420, and 430.

Location information of each of the selected pixels may be represented by polar coordinates having the center of the pupil as their origin. That is, the location information of each of the selected pixels may be specified by a distance $r_n$ from the origin and a direction $\theta_n$.

Once the location information of each of the selected pixels is specified, a matrix I is calculated based on the location information of each of the selected pixels.

Specifically, the brightnesses of pixels in the direction $\theta_\alpha°$ with respect to the center of the pupil are arranged in an uppermost row of the matrix I, and the brightnesses of pixels in directions rotated from the direction $\theta_\alpha°$ at intervals of the predefined angle are sequentially arranged in rows below the uppermost row so that the brightnesses of pixels in the direction $\theta_\beta°$ with respect to the center of the pupil can be arranged in a lowermost row of the matrix I.

The brightnesses of pixels closest to the center of the pupil are in a leftmost column of the matrix I, and the brightnesses of pixels less close to the center of the pupil are sequentially arranged in columns to the right of the leftmost column so that the brightnesses of pixels most distant from the center of the pupil can be arranged in a rightmost column of the matrix I.

The matrix I may be represented by Equation (2):

$$I = \begin{pmatrix} I_{1,1} & \cdots & I_{1,w} \\ \vdots & I_{m,n} & \vdots \\ I_{h,1} & \cdots & I_{h,w} \end{pmatrix} \quad (2)$$

where $I_{m,n}=P(r_n \cos \theta_m, r_n \sin \theta_m)$ and P denotes location information of each pixel.

Each element of the matrix I represents the brightness of a pixel. That is, each element of the matrix I may have a value of 0 to 255.

As described above, elements arranged in a first column of the matrix I represent the brightnesses of pixels close to the center of the pupil, and elements arranged in a w-th column of the matrix I represent the brightnesses of pixels close to the sclera.

Elements arranged in a first row of the matrix I represent the brightnesses of pixels in the direction $\theta_\alpha$ with respect to the center of the pupil, and elements arranged in an h-th row of the matrix I represent the brightnesses of pixels in the direction $\theta_\beta$ with respect to the center of the pupil.

Since the brightness of the sclera vastly differs from the brightness of the iris, elements of the matrix I that exhibit a large variation in brightness may be determined to correspond to the boundary between the iris and the sclera.

For example, if an element $I_{m,n}$ of the matrix I shows a large variation in brightness, a pixel corresponding to the element $I_{m,n}$ may be determined as being at the boundary between the iris and the sclera.

However, since there may be places where brightness rapidly changes, even within the iris, all selected pixels may be blurred to distinguish such places from the boundary between the iris and the sclera.

Figure 5:
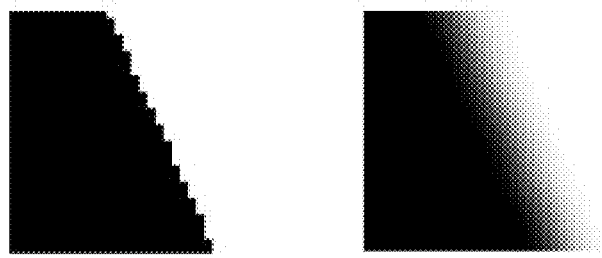
FIG. 5 is a schematic view illustrating a process of blurring selected pixels according to an exemplary embodiment of the present disclosure.

FIG. 5 is a schematic view illustrating a process of blurring selected pixels according to an exemplary embodiment of the present disclosure.

Blurring is a type of image processing for reducing differences in brightness between pixels adjacent to one another by using a low pass filter (LPF), an average filter, or the like.

For example, referring to FIG. 5, if blurring is applied to two groups of pixels having a large difference in brightness therebetween, the difference in brightness along the boundary between the two groups of pixels is reduced, and as a result, the boundary between the two groups of pixels may become blurry.

In a case where pixels having different brightnesses are arranged in the vicinity of each other in regions other than the boundary between the iris and the sclera, the differences in brightness between the pixels can be reduced by blurring, and as a result, the boundary between the iris and the sclera can be precisely detected because the difference in brightness between the iris and the sclera remains huge even after blurring.

Thereafter, the boundary between the iris and the sclera is detected from an image obtained by blurring.

Figure 6:
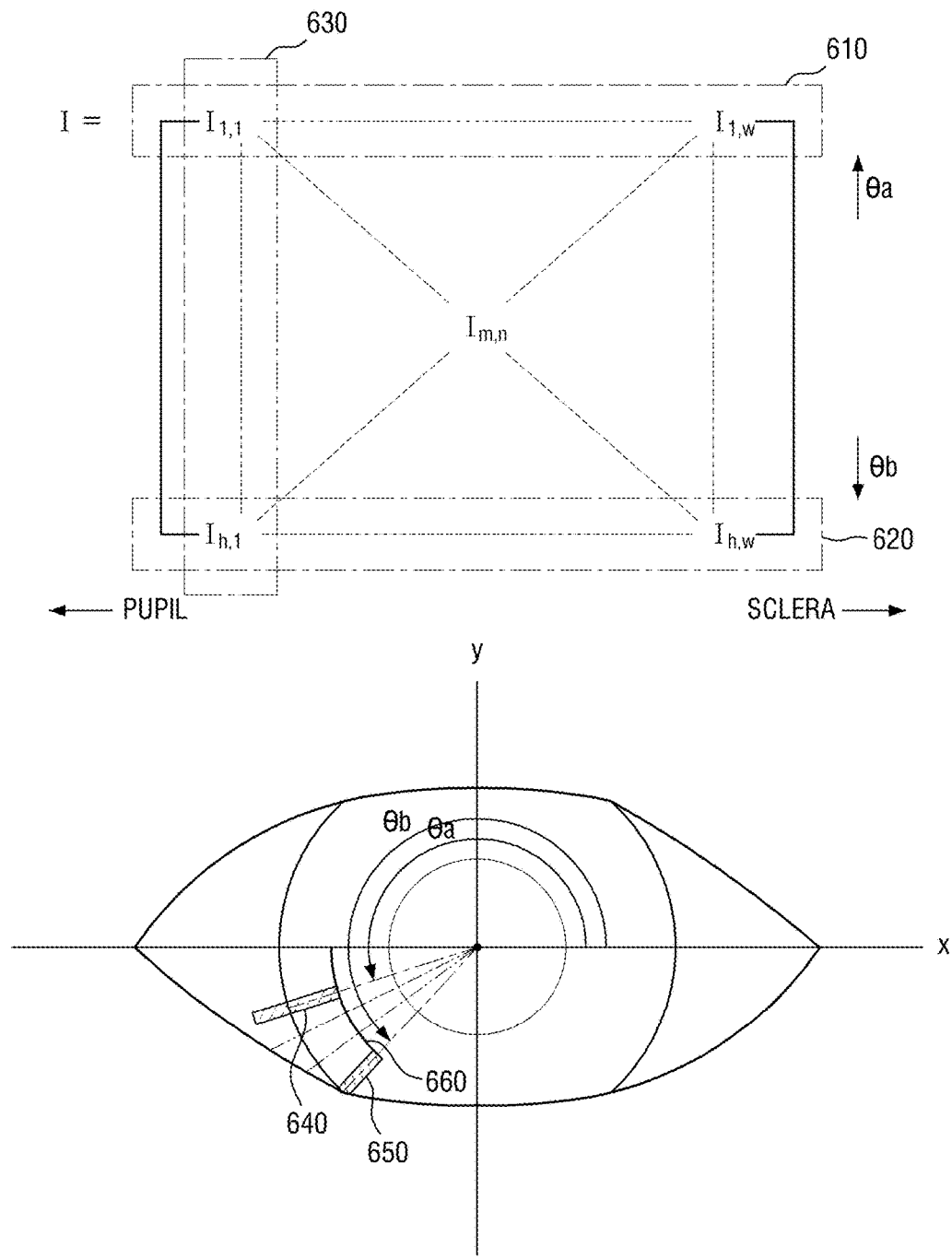
FIG. 6 is a schematic view illustrating a process of detecting the boundary between the iris and the sclera according to an exemplary embodiment of the present disclosure.

FIG. 6 is a schematic view illustrating a process of detecting the boundary between the iris and the sclera according to an exemplary embodiment of the present disclosure.

As described above, left columns of the blurred matrix I represent pixels in the direction of the pupil in the captured image of the user's eye area, and right columns of the matrix I represent pixels in the direction of the sclera in the captured image of the user's eye area.

That is, elements in a first row 610 of the matrix I represent the brightnesses of pixels in the direction $\theta_\alpha$ with respect to the center of the pupil. Among the elements in the first row 610, elements close to a first column represent the brightnesses of pixels close to the pupil, and elements close to a w-th column represent the brightnesses of pixels close to the sclera.

Accordingly, the brightnesses of pixels in a first region 640 in the captured image of the user's eye area may correspond to the elements in the first row 610.

Elements in an h-th row 620 may represent the brightnesses of pixels in a second region 650 in the captured image of the user's eye area.

Elements in the same column of the matrix I may represent the brightnesses of pixels that are the same distance from the center of the pupil, but correspond to different directions with respect to the center of the pupil.

For example, the elements in a first column 630 may represent the brightnesses of pixels that are the same distance from the center of the pupil, but correspond to different directions (in the range of the direction $\theta_\alpha$ to the direction $\theta_\beta$) with respect to the center of the pupil.

Accordingly, the elements in the first column 630 may represent the brightnesses of pixels in a third region 660 in the captured image of the user's eye area.

In order to detect the boundary between the iris and the sclera, elements that exhibit a large variation in brightness may be detected by sequentially scanning through the brightnesses of pixels in each row of the matrix I.

The elements in each column of the matrix I are the same distance from the center of the pupil, but correspond to different directions with respect to the center of the pupil, as indicated by the third region 660. Thus, the elements in each column of the matrix I do not include boundary information. However, the elements in each row of the matrix I represent the brightnesses of pixels arranged sequentially in a direction from the center of the pupil to the sclera, as indicated by the first and second regions 640 and 650, and thus include boundary information.

It will hereinafter be described how to detect the boundary between the iris and the sclera by comparing the values of the elements in each row of the matrix I.

Figure 7:
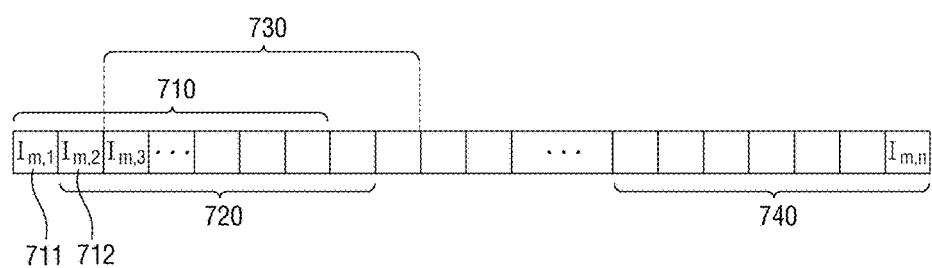
FIG. 7 is a schematic view illustrating a process of detecting variations in brightness from each row of pixels according to an exemplary embodiment of the present disclosure.

FIG. 7 is a schematic view illustrating a process of detecting variations in brightness from each row of pixels according to an exemplary embodiment of the present disclosure.

Pixels that are in the same direction with respect to the center of the pupil are selected to detect a variation in brightness from the rows of the matrix I, and a pixel group is formed by selecting only a predefined number of pixels from among the selected pixels. FIG. 7 shows pixels corresponding to elements in an arbitrary row (i.e., an m-th row) of the matrix I. Elements in the same row of the matrix I correspond to the same direction with respect to the center of the pupil. Thus, by selecting a row of elements from the matrix I, pixels that are in the same direction with respect to the center of the pupil can be selected.

Once pixels that are in the same direction with respect to the center of the pupil are selected, a pixel group is formed by selecting only a predefined number of pixels from the pixels selected from among the selected pixels.

For example, referring to FIG. 7, a first pixel group 710 is formed by selecting seven pixels. Then, a second pixel group 720 is formed by selecting seven pixels including some of the seven pixels included in the first pixel group 710.

The formation of a pixel group is continued until all the elements in each row of the matrix I, i.e., each group of pixels in the same direction with respect to the center of the pupil, are selected at least once.

Thereafter, the feature value of each pixel group is calculated by comparing the brightnesses of each pair of adjacent pixels included in the corresponding pixel group.

To calculate the feature value of a pixel group, the difference between the brightness of each pixel included in the pixel group and the brightness of a pixel adjacent thereto to the right is calculated.

For example, the difference between the brightness of a first pixel 711 in the first pixel group 710 and the brightness of a second pixel 712 adjacent to the first pixel 711 to the right is calculated using Equation (3):

$$G_{m,n} = I_{m,n} - I_{m,n+1} \quad (3)$$

Thereafter, if the difference between the brightnesses of the first and second pixels 711 and 712 is positive, a value of 1 is allocated to the first pixel group 710, and if the difference between the brightnesses of the first and second pixels 711 and 712 is negative, a value of −1 is allocated to the first pixel group 710.

For example, if the first pixel 711 has a brightness of 10 and the second pixel 712 has a brightness of 20, a value of −1 is allocated to the first pixel group 710 as the value of $G_{1,1}$. On the other hand, if the first pixel 711 has a brightness of 20 and the second pixel 712 has a brightness of 13, a value of 1 is allocated to the first pixel group 710 as the value of $G_{1,1}$.

This process may be expressed by Equation (4):

$$G_{m,n} = \begin{cases} 1, & (G_{m,n} > 0) \\ -1 & (G_{m,n} < 0) \end{cases}. \quad (4)$$

The process represented by Equation (4) is applied to all pixels in each pixel group. If there are x pixels in the first pixel group 710, a total of (x−1) $G_{m,n}$ values may be obtained for the first pixel group 710.

Then, the sum of all the values allocated to a pixel group is determined as the feature value of the pixel group.

A feature value $M_K$ of a pixel group may be calculated by Equation (5);

$$M_k = \sum_{n=-1}^{1} G_{m,n+l+k-1} (1 \le k \le w - 21). \quad (5)$$

Thereafter, a pixel group having a largest feature value is detected. A pixel group having a largest feature value is a pixel group having pixels that exhibit a largest variation in brightness therebetween. A pixel having a largest feature value is highly likely to include a pixel corresponding to the boundary between the iris and the sclera.

FIG. 7 illustrates detecting a pixel group having a largest feature value from only one row of the matrix I, but the process of FIG. 7 may be applied to all the rows of the matrix I.

Therefore, if there are h rows in the matrix I, a pixel group having a largest feature value may be detected from each of the h rows, and a pixel corresponding to the boundary between the iris and the sclera may be detected from each of the detected pixel groups.

Figure 8:
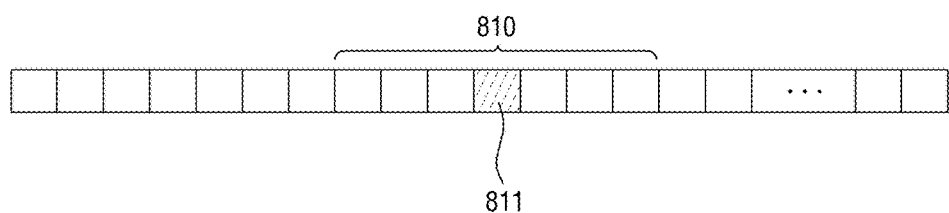
FIG. 8 is a schematic view illustrating a process of detecting a pixel corresponding to the boundary between the iris and the sclera from a pixel group having a largest feature value according to an exemplary embodiment of the present disclosure.

FIG. 8 is a schematic view illustrating a process of detecting a pixel corresponding to a boundary from a pixel group having a largest feature value according to an exemplary embodiment of the present disclosure.

Once a pixel group having a largest feature value is detected, the sum of the brightnesses of pixels to the left of each pixel and the sum of the brightnesses of pixels to the right of the corresponding pixel are calculated, starting from a pixel at the center of the pixel group and proceeding in sequence to the pixels to the left of the center pixel.

For example, referring to FIG. 8, if a third pixel group 810 is a pixel group having a largest feature value, the sum of the brightnesses of pixels to the left of a center pixel 811 of the third pixel group 810 and the sum of the brightnesses of pixels to the right of the center pixel 811 are calculated.

This calculation process proceeds in sequence to the pixels to the left of the center pixel 811.

This calculation process may be expressed by Equation (6):

$$L_i = \sum_{n=-1}^{0} I_{m,j-(n+l+1)}, \; R_1 = \sum_{n=0}^{1} I_{m,j-(n-l+1)}, \; (0 \le i \le j - l). \quad (6)$$

Thereafter, a pixel that satisfies $L_i < R_i$ is searched for. The color of pixels close to the center of the pupil is likely to be close to black, and the color of pixels close to the sclera is likely to be close to white.

Also, pixels close to the left of FIG. 8 are likely to be close to the center of the pupil, and the pixels close to the right of FIG. 8 are likely to be close to the sclera.

If there are multiple pixels satisfying Li<Ri, a pixel having a largest Ri/Li is determined to be a pixel corresponding to the boundary between the iris and the sclera. That is, any arbitrary pixel having a largest difference between the sum of the brightnesses of pixels to its left and the sum of the brightnesses of pixels to its right is determined to be a pixel corresponding to the boundary between the iris and the sclera.

The process of FIG. 8 may be applied to all the rows of the matrix I. If there are h rows in the matrix I, a total of h pixels may be detected as pixels corresponding to the boundary between the iris and the sclera, and a boundary line representing the boundary between the iris and the sclera may be obtained by connecting the detected pixels to one another.

However, the boundary line obtained by connecting the detected pixels to one another may not be smooth, but may be jagged.

Figure 9:
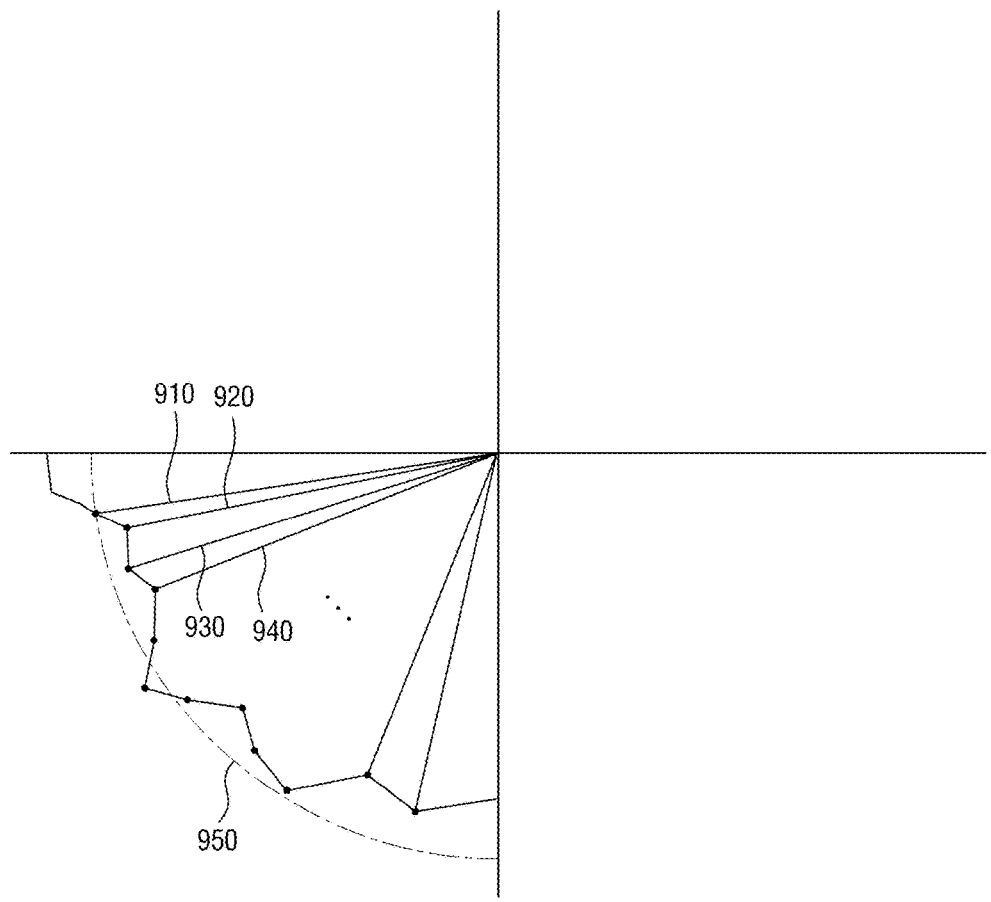
FIG. 9 is a schematic view illustrating a process of correcting the boundary between the iris and the sclera according to an exemplary embodiment of the present disclosure.

FIG. 9 is a schematic view illustrating a process of correcting a boundary line corresponding to the boundary between the iris and the sclera according to an exemplary embodiment of the present disclosure.

A pixel corresponding to the boundary between the iris and the sclera can be detected in each direction with respect to the center of the pupil by the processes of FIGS. 2, 3, 5, 6, 7, and 8.

For example, referring to FIG. 9, three pixels may be detected in first, second, and third directions 910, 920, and 930, respectively, with respect to the center of the pupil as pixels corresponding to the boundary between the iris and the sclera.

These detected pixels may have different distances from the center of the pupil. Thus, a boundary line obtained by connecting the detected pixels to one another may be jagged.

Accordingly, the method of detecting the boundary between the iris and the sclera according to an exemplary embodiment of the present disclosure may correct a jagged boundary line, thereby obtaining a smooth boundary line.

To this end, one of the detected pixels is selected, and the differences in distance from the center of the pupil between the selected pixel and the other detected pixels are calculated.

For example, the difference between the distance between the pixel detected in the first direction 910 and the center of the pupil and the distance between the pixel detected in the second direction 920 and the center of the pupil is calculated.

Thereafter, the difference between the distance between the pixel detected in the first direction 910 and the center of the pupil and the distance between the pixel detected in the third direction 930 and the center of the pupil is calculated.

Then, the number of differences calculated to be smaller than a predefined threshold value is calculated, and one of the detected pixels having a largest number of differences calculated to be smaller than the predefined threshold value is determined as a pixel corresponding to the boundary between the iris and the sclera.

For example, if the pixel detected in the first direction 910 has ten differences calculated to be smaller than the predefined threshold value and the other detected pixels have less than ten differences calculated to be smaller than the predefined threshold value, the distance between the pixel detected in the first direction 910 and the center of the pupil may be determined as the distance between the center of the pupil and the boundary between the iris and the sclera.

Thereafter, a circle having the distance between the pixel detected in the first direction 910 and the center of the pupil as its radius may be determined as a boundary line 950 corresponding to the boundary between the iris and the sclera.

By using the process of FIG. 9, a smooth boundary line can be obtained.

Also, the boundary between the iris and the sclera can be quickly and precisely detected, compared to using a conventional circular boundary detector.

Figure 10:
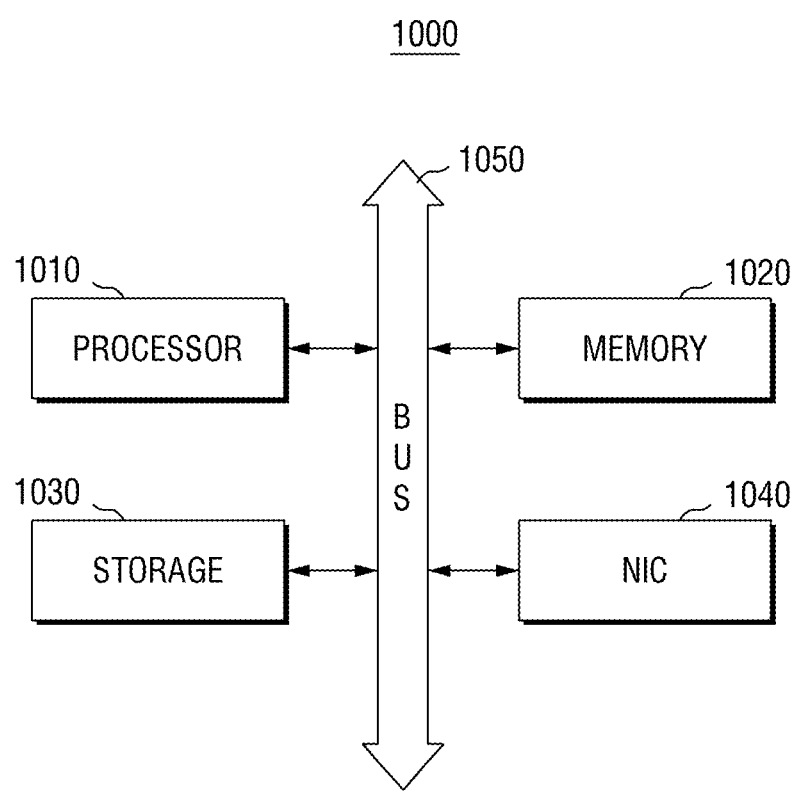
FIG. 10 is a block diagram illustrating an apparatus for detecting the boundary between the iris and the sclera according to an exemplary embodiment of the present disclosure.

FIG. 10 is a block diagram illustrating an apparatus for detecting the boundary between the iris and the sclera according to an exemplary embodiment of the present disclosure.

Referring to FIG. 10, an apparatus 1000 for detecting the boundary between the iris and the sclera includes a processor 1010, a memory 1020, a storage 1030, a network interface "NIC" 1040, and a bus 1050.

FIG. 10 illustrates only components relevant to exemplary embodiments of the present disclosure, but it is obvious to a person skilled in the art that the apparatus 100 may also include other universal components.

The processor 1010 executes a program capable of detecting the boundary between the iris and the sclera. However, the type of program that can be executed by the processor 1010 is not particularly limited, and other universal programs can be executed by the processor 1010.

The storage 1020 stores the program for detecting a pupil center therein. According to an exemplary embodiment of the present disclosure, the program for detecting the boundary between the iris and the sclera, when executed, causes a computer to perform an operation of receiving a captured image of a user's eye area; an operation of selecting pixels included in a predefined region of the received image; an operation of selecting pixels in the same direction with respect to the center of the pupil from the selected pixels from the predefined region; an operation of creating one or more pixel groups by selecting a predefined number of pixels from the selected pixels in the same direction with respect to the center of the pupil; an operation of calculating a feature value of each of the pixel groups by comparing brightnesses of each pair of adjacent pixels included in a corresponding pixel group; an operation of selecting a pixel group having a largest feature value and calculating a first sum of brightnesses of pixels to the left of each pixel in the selected pixel group and a second sum of brightnesses of pixels to the right of a corresponding pixel, starting from a pixel at the center of the selected pixel group and proceeding in sequence to the pixels to the left of the center pixel; and an operation of determining one or more pixels having a larger first sum than a second sum as pixels corresponding to the boundary between the iris and the sclera.

The memory 1020 may load the program for detecting a pupil center so that the program is executed on the processor 1010.

The network interface card(NIC) 1040 may be connected to a computing device.

The bus 1050 works as a data transfer path among the processor 1010, the storage 1020, the memory 1020, and the network interface card(NIC) 1040.

The above-described method may be implemented as a program that can be executed by a computer, and may be embodied in a computer-readable storage medium to be performed in a general-purpose digital computer that executes the program. In addition, the structure of the data used in the above-described method may be written on a computer-readable storage medium through various means. The computer-readable storage medium includes a storage medium such as a magnetic storage medium (e.g., a ROM, a floppy disk, a hard disk, etc.), and an optical recording medium (e.g., CD-ROM, a DVD, etc.).

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of detecting the boundary between the iris and the sclera, comprising:
   receiving a captured image of a user's eye area;
   selecting pixels included in a predefined region of the received image;
   selecting pixels in the same direction with respect to the center of the pupil from among the selected pixels from the predefined region;
   creating one or more pixel groups by selecting a predefined number of pixels from among the selected pixels in the same direction with respect to the center of the pupil;
   calculating a feature value of each of the pixel groups by comparing brightnesses of each pair of adjacent pixels included in a corresponding pixel group;
   selecting a pixel group having a largest feature value and calculating a first sum of brightnesses of pixels to the left of each pixel in the selected pixel group and a second sum of brightnesses of pixels to the right of a corresponding pixel, starting from a pixel at the center of the selected pixel group and proceeding in sequence to the pixels to the left of the center pixel; and
   determining one or more pixels having a larger first sum than a second sum as pixels corresponding to the boundary between the iris and the sclera.

2. The method of claim 1, wherein the selecting the pixels included in the predefined region, comprises selecting pixels in a range of a direction $\theta_\alpha°$ to a direction $\theta_\beta°$ with respect to the center of the pupil at intervals of a predefined angle and selecting a number of pixels corresponding to a predetermined length from among the selected pixels in the range of the direction $\theta_\alpha°$ to the direction $\theta_\beta°$ with respect to the center of the pupil, starting from a pixel spaced a predetermined distance from the center of the pupil.

3. The method of claim 2, further comprising:
creating a matrix by arranging the brightnesses of pixels in the direction $\theta_\alpha°$ with respect to the center of the pupil in an uppermost row of the matrix and sequentially arranging the brightnesses of pixels in directions rotated from the direction $\theta_\alpha°$ at intervals of the predefined angle in rows below the uppermost row so that the brightnesses of pixels in the direction $\theta_\beta°$ with respect to the center of the pupil can be arranged in a lowermost row of the matrix, and arranging the brightnesses of pixels closest to the center of the pupil in a leftmost column of the matrix and sequentially arranging the brightnesses of pixels less close to the center of the pupil in columns to the right of the leftmost column so that the brightnesses of pixels most distant from the center of the pupil can be arranged in a rightmost column of the matrix.

4. The method of claim 3, wherein the selecting the pixels in the same direction with respect to the center of the pupil, comprises selecting pixels corresponding to elements included in the same row of the matrix.

5. The method of claim 3, wherein the creating the pixel groups, comprises (a) creating a first pixel group by selecting a predefined number of elements from each row of the matrix, (b) creating a second pixel group by selecting elements such that some of the pixels included in the first pixel group can also be included in the second pixel group, and repeatedly performing (a) and (b) so that all the elements included in each row of the matrix can be selected at least once.

6. The method of claim 1, wherein the calculating the feature value of each of the pixel groups, comprises calculating a difference between the brightness of each pixel included in each of the pixel groups and the brightness of a pixel adjacent thereto to the right, allocating a value of 1 if the calculated difference is positive and allocating a value of −1 if the calculated difference is negative, and determining a sum of all the allocated values as the feature value of each of the pixel groups.

7. The method of claim 1, wherein the selecting the pixel group having the largest feature value and the calculating the first and second sums, comprise calculating a first sum of brightnesses of a predefined number of pixels to the left of each pixel and calculating a second sum of brightnesses of a predefined number of pixels to the right of a corresponding pixel.

8. The method of claim 1, further comprising:
determining one or more pixels having a largest second sum-to-first sum ratio as the pixels corresponding to the boundary between the iris and the sclera.

9. The method of claim 1, further comprising:
calculating differences in distance from the center of the pupil between one of the determined pixels and the other determined pixels;
calculating the number of differences calculated to be smaller than a predefined threshold value for each of the determined pixels; and
determining a distance between one of the determined pixels having a largest number of differences calculated to be smaller than the predefined threshold value and the center of the pupil as a distance between the center of the pupil and the boundary between the iris and the sclera.

10. An apparatus for detecting the boundary between the iris and the sclera, comprising:
at least one processor;
a memory loading a computer program, which is executed by the processor; and
a storage storing a computer program capable of detecting the boundary between the iris and the sclera,
wherein the computer program capable of detecting the boundary between the iris and the sclera, comprises:
an operation of receiving a captured image of a user's eye area;
an operation of selecting pixels included in a predefined region of the received image;
an operation of selecting pixels in the same direction with respect to the center of the pupil from the selected pixels from the predefined region;
an operation of creating one or more pixel groups by selecting a predefined number of pixels from the selected pixels in the same direction with respect to the center of the pupil;
an operation of calculating a feature value of each of the pixel groups by comparing brightnesses of each pair of adjacent pixels included in a corresponding pixel group;
an operation of selecting a pixel group having a largest feature value and calculating a first sum of brightnesses of pixels to the left of each pixel in the selected pixel group and a second sum of brightnesses of pixels to the right of a corresponding pixel, starting from a pixel at the center of the selected pixel group and proceeding in sequence to the pixels to the left of the center pixel; and
an operation of determining one or more pixels having a larger first sum than a second sum as pixels corresponding to the boundary between the iris and the sclera.

* * * * *